United States Patent [19]

Muto et al.

[11] Patent Number: 5,756,878
[45] Date of Patent: May 26, 1998

[54] THERMAL CONDUCTIVITY MEASURING DEVICE

[75] Inventors: Hiroyuki Muto; Yasuhiro Kajio, both of Tokyo; Shoji Kamiunten; Mitsuhiko Nagata, both of Kanagawa, all of Japan

[73] Assignee: Yamatake-Honeywell Co., Ltd., Tokyo, Japan

[21] Appl. No.: 585,770

[22] Filed: Jan. 16, 1996

[30] Foreign Application Priority Data

Jan. 24, 1995 [JP] Japan .................. 7-008970

[51] Int. Cl.⁶ .................................... G01N 25/18
[52] U.S. Cl. .......................... 73/25.03; 374/44
[58] Field of Search ................. 73/25.03, 204.26, 73/203.5, 204.23; 374/44; 364/571.03

[56] References Cited

U.S. PATENT DOCUMENTS

| | | | |
|---|---|---|---|
| 4,080,821 | 3/1978 | Johnston | 73/27 R |
| 4,471,647 | 9/1984 | Jerman et al. | 73/23 |
| 4,682,503 | 7/1987 | Higashi et al. | 73/755 |
| 4,706,061 | 11/1987 | Johnson . | |
| 4,850,714 | 7/1989 | Wiegleb | 374/44 |
| 4,902,138 | 2/1990 | Gouldman et al. . | |
| 4,944,035 | 7/1990 | Aagardl et al. | 364/556 |
| 4,956,793 | 9/1990 | Bonne et al. | 364/558 |
| 5,117,696 | 6/1992 | Bonne | 374/44 |
| 5,237,523 | 8/1993 | Bonne et al. | 374/44 |
| 5,295,389 | 3/1994 | Nagata et al. . | |
| 5,303,167 | 4/1994 | Bonne . | |
| 5,377,527 | 1/1995 | Kamiunten | 73/25.03 |
| 5,463,899 | 11/1995 | Zemel et al. | 73/195 |
| 5,515,295 | 5/1996 | Wang | 73/204.26 |
| 5,515,714 | 5/1996 | Sultan et al. | 73/25.01 |

FOREIGN PATENT DOCUMENTS

| | | |
|---|---|---|
| 382414 | of 1990 | European Pat. Off. . |
| 2209413 | of 1973 | Germany . |
| 3711511 | of 1988 | Germany . |
| 58-202863 | 11/1983 | Japan . |

OTHER PUBLICATIONS

"Development of Calorie Transmitter For Quick Response Calorific Value Control" by M. Seto et al., IGRC95.

Primary Examiner—Hezron E. Williams
Assistant Examiner—Jay L. Politzer
Attorney, Agent, or Firm—Laurence J. Marhoefer

[57] ABSTRACT

A thermal conductivity measuring device includes a diaphragm portion, a thermal conductivity detector, a temperature sensor, a control section, and a thermal conductivity calculating section. The diaphragm portion is formed on a base. The thermal conductivity detector is formed in the diaphragm portion to perform conduction of heat to/from a sample gas. The temperature sensor is disposed on the base to be near the thermal conductivity detector so as to measure the ambient temperature around the base. The temperature sensor is thermally insulated from the thermal conductivity detector. The control section controls the amount of energy supplied to the thermal conductivity detector such that the temperature difference between the ambient temperature measured by the temperature sensor and the heating temperature of the thermal conductivity detector becomes a constant value. The thermal conductivity calculating section calculates the thermal conductivity of the sample gas on the basis of the amount of energy supplied to the thermal conductivity detector while the temperature difference is kept at the constant value by the control section.

10 Claims, 7 Drawing Sheets

THERMAL CONDUCTIVITY MEASURING DEVICE

BACKGROUND OF THE INVENTION

The present invention relates to a thermal conductivity measuring device suitably used for a thermal conductivity type gas analyzer.

PRIOR ART 1

Figure 8:
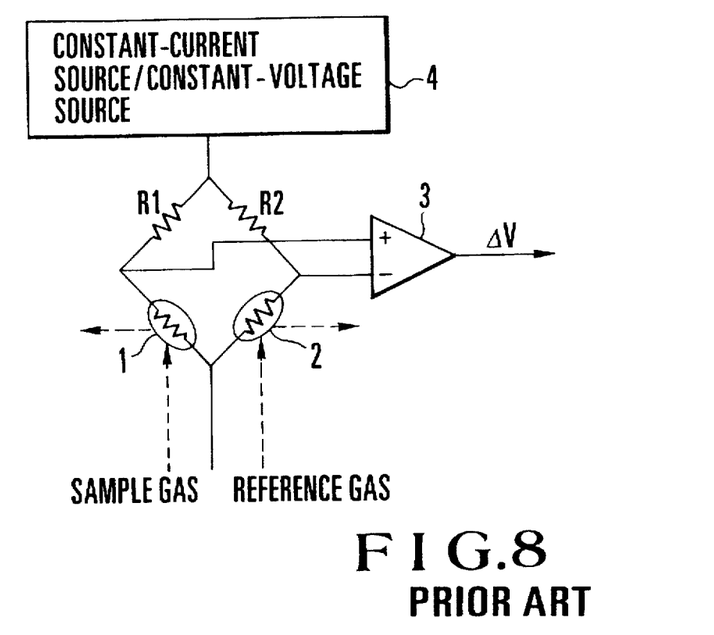
FIG. 8 is a circuit diagram showing the arrangement of the main part of a conventional thermal conductivity type hydrogen meter.

As a thermal conductivity type gas analyzer used in an oil refining, petrochemical, or steel plant, a thermal conductivity type hydrogen meter whose main part is shown in FIG. 8 has been used. Referring to FIG. 8, reference numeral 1 denotes a first thermal conductivity detector (to be referred to as a TCD hereinafter) disposed in a supply path for a sample gas (e.g., a gas containing $H_2$ gas as a measurement gas and $N_2$ gas as a carrier gas); 2, a second TCD disposed in a supply path for a reference gas whose thermal conductivity is known; R1 and R2, resistors, 3, a comparator; and 4, a constant-current source/constant-voltage source. As the TCDs 1 and 2, platinum filaments are generally used. The TCDs 1 and 2 and the resistors R1 and R2 constitute a Wheatstone bridge.

In this thermal conductivity type hydrogen meter, a sample gas is supplied to the TCD 1, and deprives the TCD 1 of heat in proportion to its thermal conductivity. As a result, the heating temperature of the TCD 1 changes, and its resistance value changes. Meanwhile, a reference gas is supplied to the TCD 2. In this case, since the thermal conductivity of the reference gas is constant, the heat deprived from the TCD 2 by the reference gas is also constant. Consequently, the heating temperature of the TCD 2 is constant, and its resistance value is constant.

A voltage generated at the connection point between the resistor R1 and the TCD 1 is applied to the non-inverting input of the comparator 3, and a voltage generated at the connection point between the resistor R2 and the TCD 2 is applied to the inverting input of the comparator 3. With this operation, a resistance value change proportional to the difference in thermal conductivity between the sample gas and the reference gas is detected as unbalanced voltage $\Delta V$. In this case, if the reference gas has the same component ($N_2$ gas) as that of a carrier gas contained in the sample gas, the concentration of $H_2$ gas contained in the sample gas can be measured by referring to a calibration curve preset on the basis of the detected unbalanced voltage $\Delta V$.

PRIOR ART 2

Figure 9:
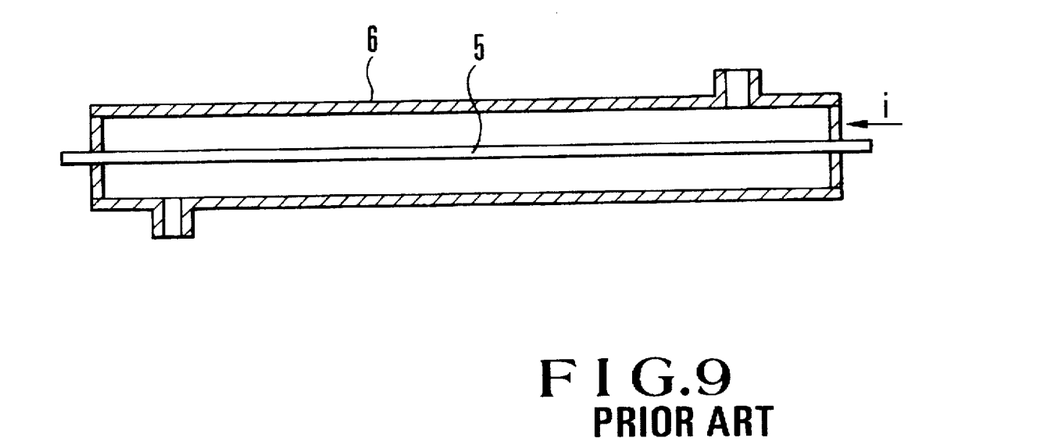
FIG. 9 is a view for explaining the principle of a conventional two-constant temperature type thermal conductivity measurement cell.

FIG. 9 shows the principle of a two-constant temperature type thermal conductivity measurement cell disclosed in Japanese Patent Laid-Open No. 58-202863. Referring to FIG. 9, reference numeral 5 denotes a temperature measuring resistance wire consisting of a thin platinum wire; and 6, a vessel made of a cylindrical metal outer tube. The temperature measuring resistance wire 5 is stretched in the center of the vessel 6. In this two-constant temperature type thermal conductivity measurement cell, a sample gas is fed into the vessel 6 as a measurement chamber, and the temperature in the vessel 6 is kept at a predetermined temperature $t_2°C$. In this state, a current i is supplied to the temperature measuring resistance wire 5 to set the temperature of the temperature measuring resistance wire 5 at a predetermined temperature $t_1°C$. The thermal conductivity of the sample gas is obtained by measuring the current i.

PRIOR ART 3

Figure 10:
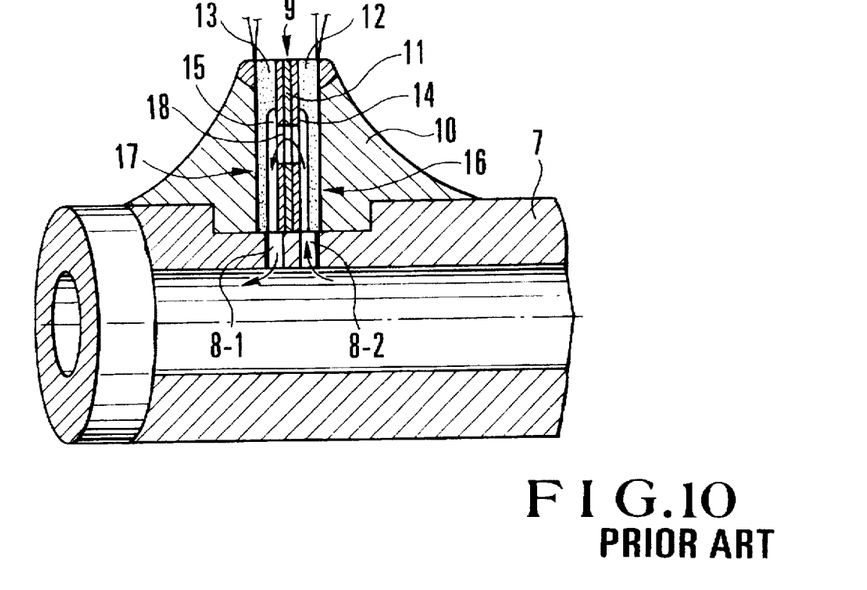
FIG. 10 is a sectional view showing the main part of a conventional gas thermal conductivity measuring device.

FIG. 10 shows the main part of a gas thermal conductivity measuring device disclosed in U.S. Pat. No. 4,850,714.

Referring to FIG. 10, reference numeral 7 denotes a main flow pipe; 8-1 and 8-2, radial branch bores 8-1 and 8-2; 9, a measurement cell; 10, a compound; 11, a base block; 12 and 13, ceramic plates; 14 and 15, flow channels; 16 and 17, heating resistors; and 18, a window. The heating resistors 16 and 17 are formed, as platinum thin resistors, on the outer surfaces of the ceramic plates 12 and 13, and are used as measurement resistors for controlling the measurement cell 9 at a constant temperature.

Figure 11A:
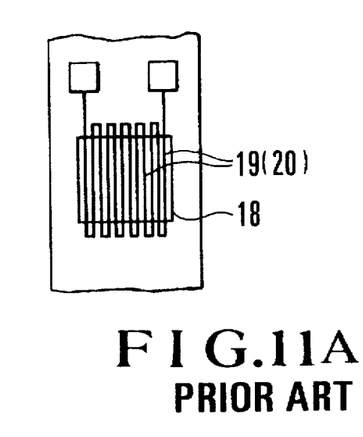
FIGS. 11A and 11B are plan and sectional views showing the structure of the base block of the conventional device in FIG. 10.
Figure 11B:
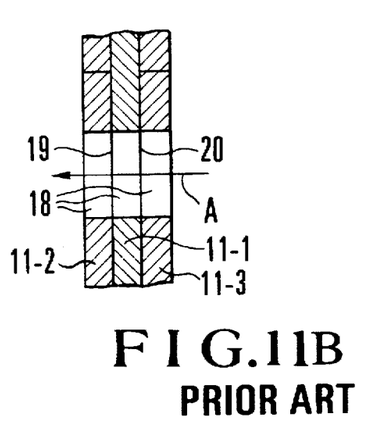

As shown enlarged in FIG. 11B, the base block 11 is constituted by a central small insulating plate 11-1 and small insulating plates 11-2 and 11-3 disposed to sandwich the central small insulating plate 11-1. The almost square window 18 is formed to extend through the small insulating plates 11-2 and 11-3. As shown in FIG. 11A, two measurement resistors 19 and 20, each having a meandering form (manufactured by masking and chemically etching a 5-µm thick small nickel plate), are formed on both sides of the central small insulating plate 11-1 to cross the window 18 many times and oppose each other.

Figure 12:
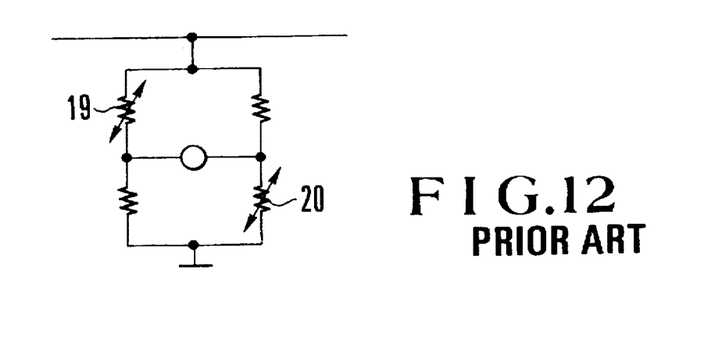
FIG. 12 is a circuit diagram showing the bridge of the convention device in FIG. 10.

Referring to FIG. 11B, an arrow A indicates a flow channel for a sample gas, and the measurement resistors 20 and 19 are respectively disposed on the upstream and downstream sides of the flow channel A. As shown in FIG. 12, the measurement resistors 19 and 20 are electrically disposed in opposing sides of the bridge. In this gas thermal conductivity measuring device, when the flow velocity is zero, temperature distributions are directly formed around the measurement resistors 19 and 20 to be symmetrical about the boundary surface between the measurement resistors 19 and 20. With a flow velocity other than zero, the peaks of the temperature distributions move in the direction of the measurement resistor 19 on the downstream side by additional thermal conduction. The difference in resistance value between the measurement resistors 19 and 20 which is caused by this temperature difference is a measure of the flow velocity or thermal conductivity of the sample gas. With this measure, the thermal conductivity of the sample gas in the flow channel A can be obtained from a voltage measured across the bridge diagonal positions.

The following problems are posed in the thermal conductivity type hydrogen meter as prior art 1:

① Since filaments are used as the TCDs 1 and 2, the volume of the analyzer cell (measurement cell+comparison cell) becomes large. As a result, gas replacement is slow. This means slow response.

② Since the TCDs 1 and 2 are thin wires, they are susceptible to vibrations (have low resonance points and are liable to disconnection).

③ Since a change in the temperature of the TCD 1 is used as an sensor output, measurement cannot be started until the change in the temperature of the TCD 1 is stabilized, resulting in poor response characteristics.

④ Since the TCD 1 undergoes large temperature changes, a thermal stress acts thereon. As a result, large resistance value drifts occur, and the service life of the meter is shortened.

⑤ Since the thermal conductivity is a function of temperature, it is important to specify a temperature at which measurement is performed. However, since the heating temperature of the TCD 1 and the difference between the heating temperature of the TCD 1 and the ambient temperature change, the thermal conductivity at a specific temperature cannot be measured. As a result, a deterioration in precision occurs.

The following problems are posed in the two-constant temperature type thermal conductivity measurement cell as prior art 2:

① Since a platinum wire or the like is used as the temperature measuring resistance wire 5, the volume of the measurement cell is large, and gas replacement is slow. For this reason, this device has poor response characteristics.

② Since the temperature measuring resistance wire 5 is a thin wire, it is susceptible to vibrations (has a low resonance point and is liable to disconnection).

③ The reference reads that the temperature of the vessel 6 is controlled to be kept at the predetermined temperature $t_2$°C. However, according to the structure of prior art 2, it is practically difficult to make the temperature of the vessel 6 uniform.

④ The reference asserts that a current is supplied to the temperature measuring resistance wire 5 to set its temperature at the predetermined temperature $t_1$°C. However, since the temperature measuring resistance wire 5 and the vessel 6 are not thermally insulated from each other, a large quantity of heat escapes from the temperature measuring resistance wire 5 to the vessel 6. It is therefore very difficult to stably control the temperature measuring resistance wire 5 at the temperature $t_1$°C.

⑤ A large temperature distribution is formed in the temperature measuring resistance wire 5.

⑥ Since the temperature of the vessel 6 interferes with the temperature of the temperature measuring resistance wire 5, the temperatures of the two are not stabilized.

⑦ Since the temperature measuring resistance wire 5 is disposed in the center of the vessel 6, the wire is easily influenced by a gas flow. For this reason, a large measurement error is produced.

⑧ Since the temperature measuring resistance wire 5 and the vessel 6 are not thermally insulated from each other, a large quantity of heat escapes from the temperature measuring resistance wire 5 to the vessel 6, resulting in poor measurement precision.

The following problems are posed in the gas thermal conductivity measuring device as prior art 3:

① Since the measurement resistors 19 and 20 are thin, and cross the window 18 many times to have meandering forms, they are susceptible to vibrations (have low resonance points and are liable to disconnection).

② Since the measurement resistors 19 and 20 cross the window 18 many times to have meandering forms, they directly receive gas flows. Since the fluid resistances are large, the resistors are liable to damage. In addition, the measurement resistors 19 and 20 are easily influenced by gas flows, and this device has an arrangement for compensating for the influences of the gas flows. However, a large thermal conductivity measurement error is produced.

③ Since changes in the temperatures of the measurement resistors 19 and 20 are used as sensor outputs, measurement has to be delayed until the changes in the temperatures of the measurement resistors 19 and 20 are stabilized, resulting in poor response characteristics.

④ The temperatures of the measurement resistors 19 and 20 greatly change, and thermal stress acts thereon. As a result, large resistance value drifts are caused, and the service life of the meter is shortened.

⑤ Since the thermal conductivity is a function of temperature, it is important to specify a temperature at which measurement is performed. However, since the heating temperatures of the measurement resistors 19 and 20 and the differences between the heating temperatures of the measurement resistors 19 and 20 and the ambient temperatures change, the thermal conductivity at a specific temperature cannot be measured. As a result, a deterioration in precision occurs.

SUMMARY OF THE INVENTION

It is an object of the present invention to provide a high-precision thermal conductivity measuring device with fast response and a long service life.

In order to achieve the above object according to the present invention, there is provided a thermal conductivity measuring device comprising a diaphragm portion formed on a base, heating means, formed in the diaphragm portion, for performing conduction of heat to/from a sample gas, measuring means, disposed on the base to be near the heating means, for measuring an ambient temperature around the base, the measuring means being thermally insulated from the heating means, control means for controlling an amount of energy supplied to the heating means such that a temperature difference between the ambient temperature measured by the measuring means and a heating temperature of the heating means becomes a constant value, and thermal conductivity calculating means for calculating a thermal conductivity of the sample gas on the basis of the amount of energy supplied to the heating means while the temperature difference is kept at the constant value by the control means.

DESCRIPTION OF THE PREFERRED EMBODIMENTS

Embodiments of the present invention will be described in detail below.

[First Embodiment]

Figure 1:
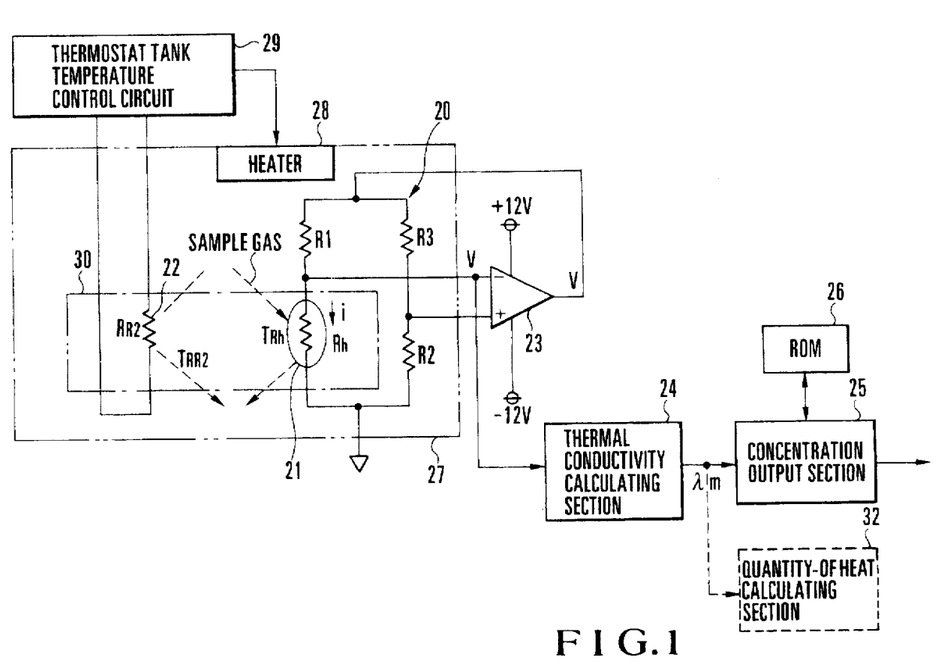
FIG. 1 is a block diagram showing the schematic circuit arrangement of a thermal conductivity type hydrogen meter according to an embodiment of the present invention.

FIG. 1 shows the schematic arrangement of a thermal conductivity measuring device of the present invention, which is applied to a thermal conductivity type hydrogen meter for calculating the concentration of hydrogen in a sample gas by measuring the thermal conductivity of the gas. Referring to FIG. 1, reference numeral 21 denotes a thermal conductivity detector (to be referred to as a TCD hereinafter) as a heating means disposed in a supply path for a sample gas (e.g., a gas containing $H_2$ gas as a measurement gas and $N_2$ gas as a carrier gas); 22, a temperature sensor as an ambient temperature measuring means; R1, R2, and R3, resistors constituting a Wheatstone resistor 20 together with the TCD 21; 23, a comparator constituted by an operational amplifier for receiving two outputs from the Wheatstone resistor 20; 24, a thermal conductivity calculating section for calculating a thermal conductivity on the basis of an output voltage from the Wheatstone resistor 20; 25, a concentration output section for outputting a gas concentration on the basis of the thermal conductivity calculated by the thermal conductivity calculating section 24; 26, a ROM (Read Only Memory) storing a plurality of calibration curves determined in accordance with gas types; 27, a thermostat tank in which the temperature sensor 22 and the Wheatstone resistor 20 are stored; 28, a heater for heating the thermostat tank 27; 29, a thermostat tank temperature control circuit for holding the thermostat tank 27 at a constant temperature by controlling the heater 28 on the basis of an output from the temperature sensor 22; and 30, a base constituted by a silicon base (to be described later) in which the TCD 21 and the temperature sensor 22 are assembled.

Figure 2:
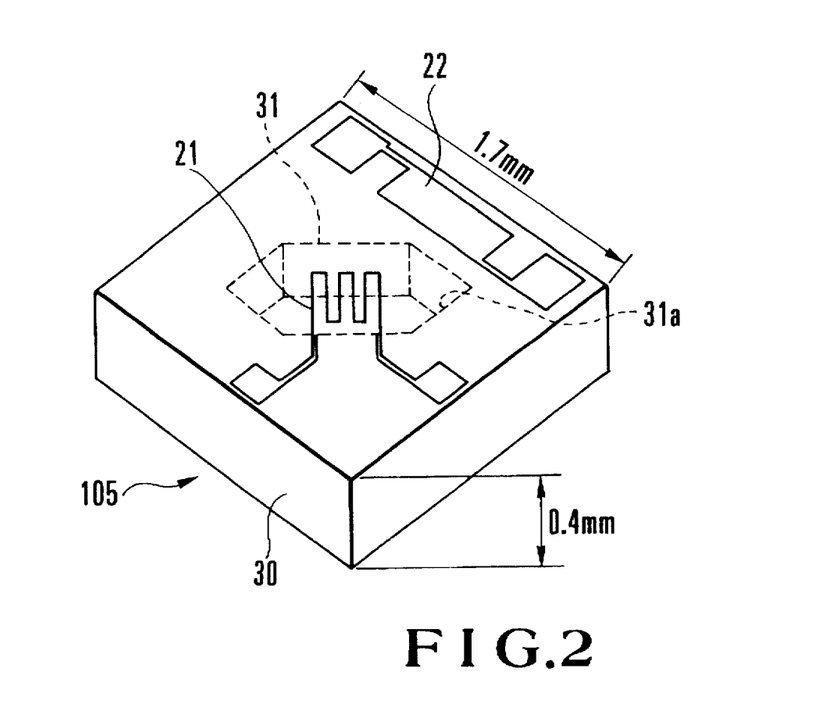
FIG. 2 is a perspective view showing a sensor chip used in the thermal conductivity type hydrogen meter in FIG. 1.

As shown in FIG. 2, the TCD 21 is formed inside a diaphragm portion 31 formed in the center of the base 30 constituting a µTCD 105 as a single-crystal silicon chip sensor, and the diaphragm portion 31 has a three-layer structure constituted by $Si_3N_4$ (silicon nitride), Pt (platinum), and $Si_3N_4$ layers. Many slits 31a are formed in the diaphragm portion 31 to allow an etching solution to pass. A space is formed under the diaphragm portion 31 by the etching solution. The temperature sensor 22 is disposed on a peripheral portion of the base 30 at a position near the TCD 21 formed inside the diaphragm portion 31. In this embodiment, the base 30 is 1.7 mm square and 0.4 mm thick.

That is, the TCD 21 is thermally insulated from the base 30, and is constituted by a thin-film resistor. The TCD 21 is therefore a high-sensitivity sensor having a very large area which comes into contact with a sample gas. In addition, since the temperature sensor 22 is disposed at a position where it is near the TCD 21 and thermally insulated therefrom, the thermal conductivity of a sample gas can be measured at a constant temperature.

Figure 3:
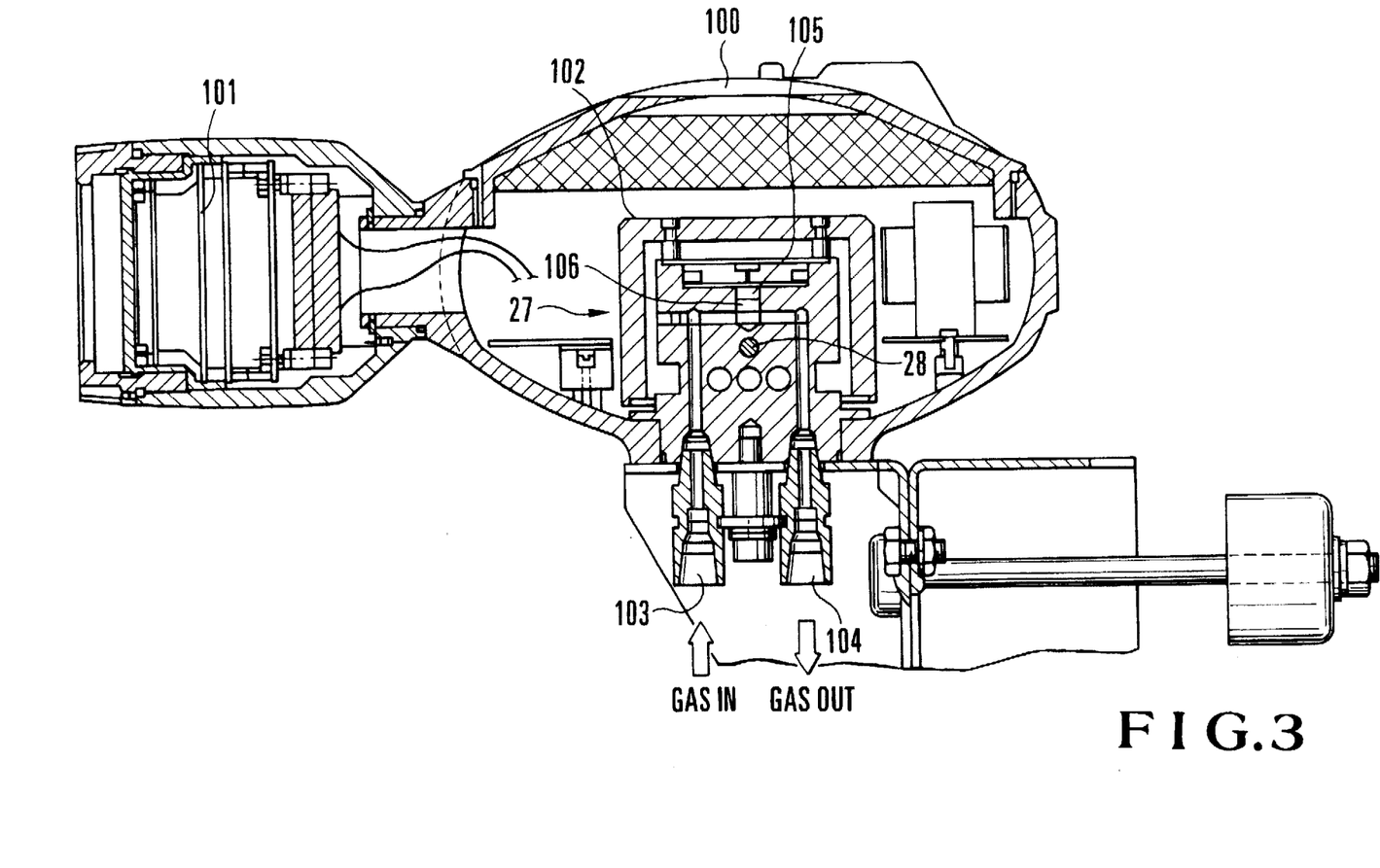
FIG. 3 is a sectional view showing the analyzer portion of the thermal conductivity type hydrogen meter.
Figure 4:
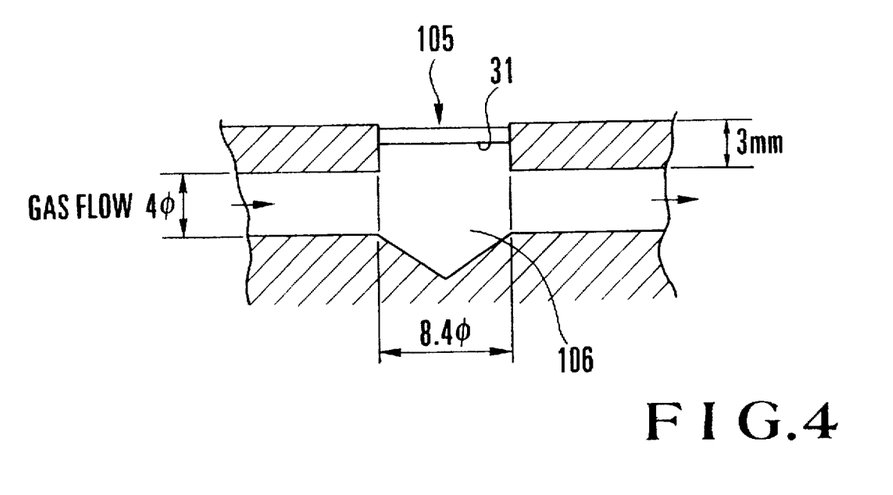
FIG. 4 is an enlarged view showing the sensor chip portion of a thermostat tank in FIG. 3.

FIG. 3 shows the main part of the analyzer portion of the thermal conductivity type hydrogen meter. Referring to FIG. 3, reference numeral 100 denotes a case; 101, a main board; 102, an oven; 103, a gas inlet; and 104, a gas outlet. The heater 28 is embedded in the oven 102 to form the thermostat tank 27. The µTCD 105 in FIG. 2 is disposed in the central portion of the thermostat tank 27 such that the diaphragm portion 31 is directed toward the supply path for a sample gas. FIG. 4 shows how the µTCD 105 is disposed in the thermostat tank 27 in FIG. 3. The volume of a chamber portion 106 facing the diaphragm portion 31 is set to be larger than that of a gas flow channel for reducing the influence of the flow of a gas.

The operation of the thermal conductivity type hydrogen meter having the above arrangement will be described next. Referring to FIG. 1, a sample gas is supplied to the TCD 21, and deprives the TCD 1 of heat in proportion to thermal conductivity. A voltage generated at the connection point between the resistor R1 and the TCD 21 is applied to the inverting input of the comparator 23, and a voltage generated at the connection point between the resistors R3 and R2 is applied to the non-inverting input of the comparator 23. The comparator 23 controls a current i supplied to the TCD 21 such that the voltage generated at the connection point between the resistor R1 and the TCD 21 becomes equal to the voltage generated at the connection point between the resistors R3 and R2, thereby keeping a resistance value Rh of the TCD 21 constant (Rh =(R1 ×R2)/R3). With this operation, a heating temperature $T_{Rh}$ of the TCD 21 is kept at a constant value, and an output voltage v changes in accordance with a change in the current i.

It is also apparent from equation (1) below that the heating temperature $T_{Rh}$ of the TCD 21 is kept at the constant value. More specifically, the TCD 21 is a platinum thin-film resistive element formed inside the diaphragm portion 31. As indicated by equation (1), if the resistance value Rh of the TCD 21 is controlled to be constant, the heating temperature $T_{rh}$ is also kept constant.

$$Rh=Rh_{20}\{1+\alpha_{20}\cdot(T_{Rh}-20)+\beta_{20}\cdot(T_{Rh}-20)^2\} \quad (1)$$

where $Rh_{20}$ is the resistance value (Ω) of the TCD 21 at 20° C., $\alpha_{20}$ is the primary resistance temperature coefficient of the TCD 21 at 20° C., and $\beta_{20}$ is the secondary resistance temperature coefficient of the TCD 21 at 20° C.

A quantity of heat $Q_T$ transferred from the TCD 21 to a neighboring portion is given by equation (2):

$$Q_T=Q_G+Q_S+Q_C+Q_R \quad (2)$$

where $Q_G$ is the quantity of heat transferred to the sample gas by thermal conduction, $Q_S$ is the quantity of heat transferred to the base 30 via the diaphragm portion 31, $Q_C$ is the quantity of heat transferred by convection (forced convection and unforced convection), and $Q_R$ is the quantity of heat transferred by radiation.

This quantity of heat $Q_T$ is also expressed by equation (3):

$$Q_T=(T_{Rh}-T_{RR2})\cdot\lambda m\cdot G+(T_{Rh}-T_{RR2})\cdot\lambda_{si}\cdot G_s+Q_C+Q_R \quad (3)$$

where $T_{RR2}$ is an ambient temperature (°C.) around the base 30, λm is the thermal conductivity (w/k·m) of the sample gas, G is a device constant (m), $\lambda_{si}$ is the thermal conductivity (w/k·m) of the diaphragm portion 31, and $G_s$ is a device constant (m) in the diaphragm portion 31.

According to equation (3), the device constant G and the device constant $G_s$ do not change regardless of the gas composition, and the quantities of heat $Q_C$ and $Q_R$ are values (or constant values) sufficiently smaller than those of the quantities of heat $Q_G$ and $Q_S$. In addition, the thermal conductivity $\lambda_{si}$ is considered as a constant value. The heating temperature $T_{Rh}$ is therefore controlled to be a constant value. In addition, the ambient temperature $T_{RR2}$ is measured by the temperature sensor 22, and power to the heater 28 is controlled by the thermostat tank temperature control circuit 29 on the basis of the measured temperature. With this operation, the temperature in the thermostat tank 27 is adjusted, and the ambient temperature $T_{RR2}$ around the base 30 is kept at a constant value. In this embodiment, the heating temperature $T_{Rh}$ and the ambient temperature $T_{RR2}$ are respectively kept at 140° C. and 60° C. With this operation, the temperature difference between the heating temperature $T_{Rh}$ and the ambient temperature $T_{RR2}$ is always kept at 80° C.

Equation (3) can therefore be rewritten as equation (4):

$$Q_T=A\cdot\lambda m+B \quad (4)$$

where A and B are device constants (shape factors including operation state factors).

The quantity of heat $Q_T$ is given by $$Q_T = i^2 \cdot Rh = v^2/Rh \tag{5}$$

Since $Q_T = A \cdot \lambda m + B = v^2/Rh$, the thermal conductivity $\lambda m$ of the sample gas is expressed by equation (6):

$$\lambda m = (v^2/Rh - B)/A \tag{6}$$

If the device constants A and B are obtained, the thermal conductivity $\lambda m$ of the sample gas can be obtained by a substitution of the output voltage v into equation (6). In this embodiment, therefore, as a mathematical expression for calculating the thermal conductivity $\lambda m$, equation (6) is set in the thermal conductivity calculating section 24. In addition, the device constants A and B in this mathematical expression are determined as follows.

A first calibration gas (e.g., 100% $N_2$ gas) whose thermal conductivity is known is supplied to the TCD 21 to measure an output voltage v ($v_{N2}$), and a second calibration gas (e.g., 100% $H_2$ gas) whose thermal conductivity is known is supplied to the TCD 21 to measure an output voltage v ($v_{H2}$). The measured output voltages $v_{N2}$ and $V_{H2}$ are then substituted into equations (7) and (8) to obtain the device constants A and B. The obtained device constants A and B are set as the device constants A and B in the mathematical expression set in the thermal conductivity calculating section 24.

$$A = (v_{N2}^2 - v_{H2}^2)/Rh \cdot (\lambda_{N2} - \lambda_{H2}) \tag{7}$$

$$B = (v_{N2}^2 \cdot \lambda_{H2} - v_{H2}^2 \cdot \lambda_{N2})/Rh \cdot (\lambda_{H2} - \lambda_{N2}) \tag{8}$$

where $\lambda_{N2}$ is the thermal conductivity (w/k·m) of 100% $N_2$ gas at $(T_{Rh} + T_{RR2})/2$, and $\lambda_{H2}$ is the thermal conductivity (w/k·m) of 100% $H_2$ gas at $(T_{Rh} + T_{RR2})/2$. Equations (7) and (8) are obtained by solving simultaneous equations (9) and (10) obtained by substitutions of $v_{N2}$, $\lambda_{N2}$, $v_{H2}$, and $\lambda_{H2}$ into $v^2 = Rh \cdot A \cdot \lambda m + Rh \cdot B$ obtained by modifying $A \cdot \lambda m + B = v^2/Rh$. In this embodiment, since the heating temperature $T_{Rh}$ and the ambient temperature $T_{RR2}$ are respectively kept at 140° C. and 60° C., $(T_{Rh} + T_{RR2})/2 = 100°$ C. Therefore, the thermal conductivities of the calibration gases, which have already been obtained as physical data at 100° C., can be used.

$$v_{N2}^2 = Rh \cdot A \cdot \lambda_{N2} + Rh \cdot B \tag{9}$$

$$v_{H2}^2 = Rh \cdot A \cdot \lambda_{H2} + Rh \cdot B \tag{10}$$

In the above case, instead of mounting the temperature sensor 22 in the base 30, a temperature sensor may be mounted in the thermostat tank 27 to keep the temperature in the thermostat tank 27 at 60° C. In this case, however, even if the temperature in the thermostat tank 27 is kept at 60° C., since different temperatures are measured at different measurement places, the ambient temperature $T_{RR2}$ around the base 30 cannot be accurately kept at 60° C. In this embodiment, the temperature sensor 22 is mounted in the base 30 to adjust the temperature in the thermostat tank 27 such that the measurement temperature of the temperature sensor 22 is kept at 60° C. The ambient temperature $T_{RR2}$ around the base 30 is accurately kept at 60° C. With this operation, the temperature difference between the heating temperature $T_{Rh}$ and the ambient temperature $T_{RR2}$ is always kept at 80° C., and hence the thermal conductivity $\lambda m$ of the sample gas can be accurately obtained by using equation (6) as a mathematical expression.

Figure 5:
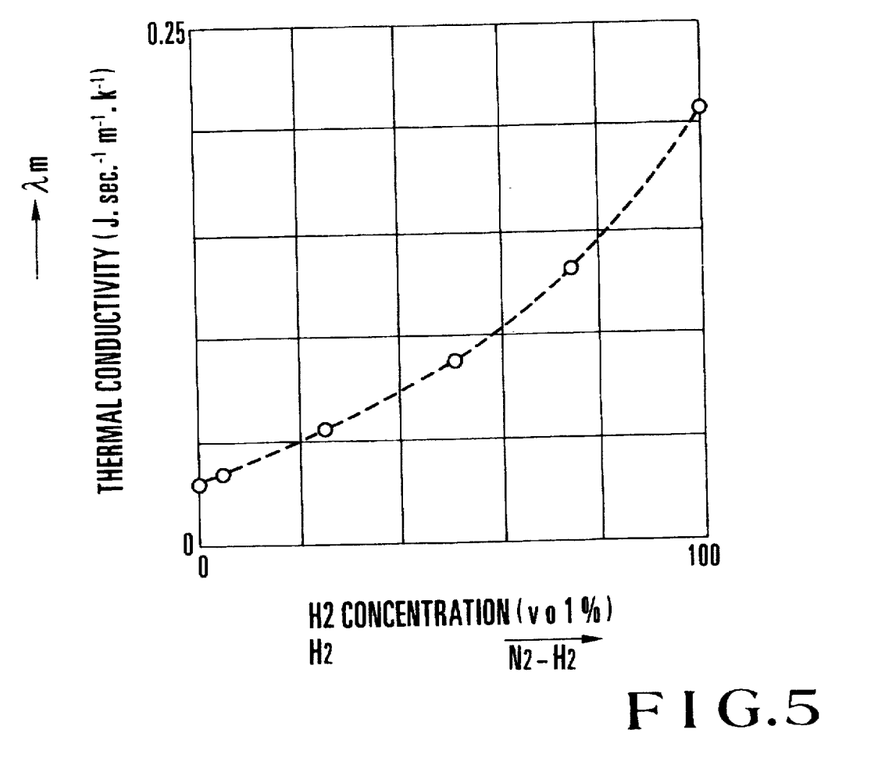
FIG. 5 is a graph showing a calibration curve stored in a ROM 26 in FIG. 1.

A plurality of types of calibration curves commonly determined for all analyzers in accordance with measurement gases and carrier gases contained in a sample gas are stored in the ROM 26. For example, various calibration curves stored in the ROM 26 include: an $N_2$—$H_2$ calibration curve representing the $H_2$ concentration of a sample gas having a thermal conductivity $\lambda m$ and containing $H_2$ as a measurement gas and $N_2$ as a carrier gas in FIG. 5; a calibration curve ($CH_4$—$H_2$ calibration curve) representing the $H_2$ concentration of a sample gas having a thermal conductivity $\lambda m$ and containing $H_2$ as a measurement gas and $CH_4$ as a carrier gas; and a calibration curve ($CO_2$—$H_2$ calibration curve) representing the $H_2$ concentration of a sample gas having a thermal conductivity $\lambda m$ and containing $H_2$ as a measurement gas and $CO_2$ as a carrier gas. In some device, these calibration curves are obtained as physical data in advance. If such calibration curves are not obtained in advance, they are created by actual measurement.

The concentration output section 25 reads out a necessary calibration curve of the calibration curves stored in the ROM 26 in accordance with the composition of a sample gas in question. In this embodiment, since $H_2$ and $N_2$ are respectively used as a measurement gas and a carrier gas, the $N_2$—$H_2$ calibration curve is read out. By using this $N_2$—$H_2$ calibration curve as reference data, the concentration of $H_2$ contained in the sample gas is obtained on the basis of the thermal conductivity $\lambda m$ of the sample gas which is calculated by the thermal conductivity calculating section 24. This concentration is then output as a measured concentration value.

With this operation, the concentration of a measurement gas can be measured without using an intrinsic calibration curve for each analyzer. In this case, as intrinsic values, the device constants A and B in the mathematical expression in the thermal conductivity calculating section 24 need only be determined on the basis of the output voltages v which are respectively measured by supplying the first and second calibration gases to the TCD 21. For this reason, the time required for calibration and adjustment of the analyzer can be greatly shortened.

In this embodiment, $H_2$ having a high thermal conductivity is used as a measurement gas. However, a gas having a high thermal conductivity, e.g., He, may be used. In contrast to this, a gas having a low thermal conductivity, e.g., $Cl_2$, may be used as a measurement gas. That is, as long as the difference in thermal conductivity between a carrier gas and a measurement gas is large, the concentration of the measurement gas can be measured in the same manner as $H_2$. Although 100% $N_2$ gas and 100% $H_2$ gas are respectively used as the first and second calibration gases, any gases can be used as calibration gases as long as their thermal conductivities are known. In addition, various calibration curves are stored in the ROM 26. However, these calibration curves may be replaced with approximate expressions to be stored. The resistance value of the heating means, i.e., heating temperature, is controlled to be constant by using the Wheatstone bridge and the operational amplifier. However, the present invention is not limited to this. For example, the resistance value of the heating means, i.e., heating temperature, may be controlled to be constant by using an arrangement constituted by a means for measuring the voltage across the two ends of the heating means, a means for supplying a current to the heating means, a microcomputer, and the like.

[Second Embodiment]

In the first embodiment, the thermal conductivity $\lambda m$ of a sample gas is calculated by substituting the output voltage v into a predetermined mathematical expression (equation (6)). However, an intrinsic v-$\lambda m$ characteristic representing the relationship between the output voltage v and the thermal conductivity $\lambda m$ may be stored for each analyzer, and the thermal conductivity $\lambda m$ corresponding to the output voltage v may be obtained from the v-$\lambda m$ characteristic.

[Third Embodiment]

Figure 6:
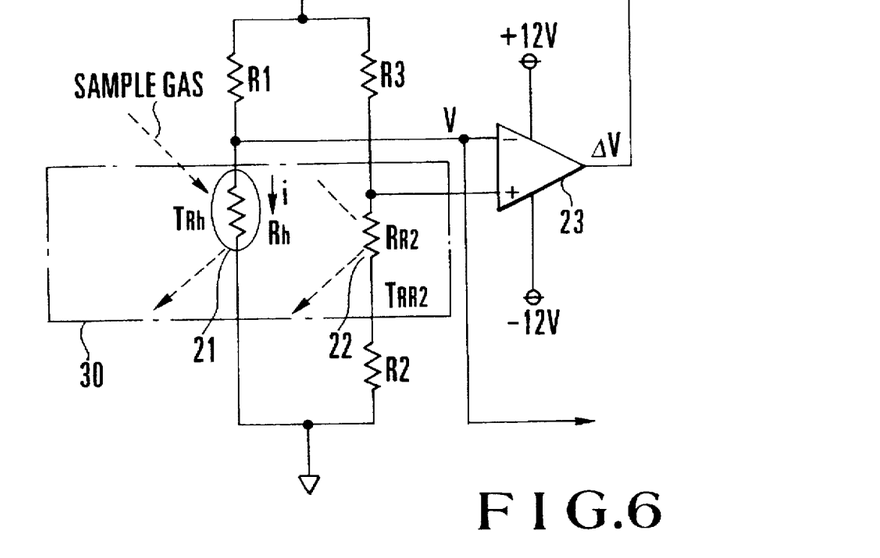
FIG. 6 is a circuit diagram showing the main part of a thermal conductivity type hydrogen meter according to another embodiment of the present invention.

In the first embodiment, the temperature in the thermostat tank 27 is adjusted such that the temperature measured by the temperature sensor 22 is kept at a constant value (60° C.). However, as shown in FIG. 6, a temperature sensor 22 may be connected between resistors R3 and R2, and the connection point between the resistor R3 and the temperature sensor 22 may be connected to the non-inverting input of a comparator 23. By setting the resistors R1, R2 and R3 to be predetermined values, a current i flowing through a TCD 21 may be controlled such that the temperature difference between a heating temperature $T_{Rh}$ of the TCD 21 and an ambient temperature $T_{RR2}$ around a base 30 becomes a constant value (80° C.).

More specifically, in the circuit shown in FIG. 6, $$R1 \times (RR2+R2) = R3 \times Rh \quad (11)$$

$$R3 \times Rh - R1 \times RR2 = R1 \times R2 \quad (12)$$

and R1×R2 is constant. The current i flowed to the TCD 21 is controlled to establish R3×Rh×R1×RR2=R1×R2 when RR2 changes. As a result, the value of Rh changes.

The ambient temperature $T_{RR2}$, therefore, does not change much. For this reason, by using this circuit, the thermal conductivity $\lambda m$ of the sample gas can be obtained with relatively high precision without using a thermostat tank 27.

A method of obtaining the resistance values of the resistors R1, R2, and R3 which make the temperature difference between the heating temperature $T_{Rh}$ of the TCD 21 and the ambient temperature $T_{RR2}$ around the base 30 constant will be described below.

A quadratic approximate expression representing the resistance values of Rh and RR2 at T [°C.] is $$R_{(T)} = R_{(20)} \cdot \{1 + \alpha_{(20)} \cdot (T-20) + \beta_{(20)} \cdot (T-20)^2\} \quad (13)$$

where $R_{(20)}$ is the resistance value at 20 [°C.], $\alpha_{(20)}$ is the primary resistance temperature coefficient at 20[°C.], and $\beta_{(20)}$ is the secondary resistance temperature coefficient at 20[°C.].

When, therefore, the heating temperature $T_{Rh}$ [°C.] of the TCD 21 is controlled to be always higher than the ambient temperature $T_{RR2}$ [°C.] around the base 30 by $\Delta T$ [°C.], i.e., to be t [°C.]=$T_{RR2}+\Delta T$, a resistance value $Rh_{(t)}$ [$\Omega$] of Rh is given by $$Rh_{(t)} = Rh_{(20)} \cdot \{1 + \alpha_{(20)} \cdot (t-20) + \beta_{(20)} \cdot (t-20)^2\} \quad (14)$$

A resistance value $RR2(T_{RR2})$ [$\Omega$] of an anbient temperature sensor RR2 at $T_{RR2}$ [°C.] is given by $$RR2(T_{RR2}) = RR2_{(20)} \cdot \{1 + \alpha_{(20)} \cdot (T_{RR2}-20) + \beta_{(20)} \cdot (T_{RR2}-20)^2\} \quad (15)$$

The balance condition for the bridge is $$Rh_{(t)} \cdot R3 = R1 \cdot (RR2(T_{RR2})+R2) \quad (16)$$

If R1=$Rh_{(t)}$ in equation (16), then R3=(RR2($T_{RR2}$)+R2).

In order to make $Rh_{(t)}$ in equation (16) equal the primary resistance change rate with respect to a temperature of (RR2($T_{RR2}$)+R2), the following equation must be satisfied:

$$(dRh_{(t)}/dt)/Rh_{(t)} = (d(RR2(T_{RR2})+R2)/dt)/(RR2(T_{RR2})+R2) \quad (17)$$

In equation (17), $$dRh_{(t)}/dt = Rh_{(20)} \cdot \{\alpha_{(20)} + 2 \cdot \beta_{(20)} \cdot (t-20)\}$$

$$d(RR72(T_{RR2})+R2)/dt = RR2_{(20)} \cdot \{\alpha_{(20)} + 2 \cdot \beta_{(20)} \cdot (T_{RR2}-20)\}$$

In this case, for example, the resistance values of the resistors R1, R2, and R3 are obtained when $T_{RR2}$=60 [°C.], $\Delta T$=80 [°C.], and t=$T_{RR2}+\Delta T$=140 [°C.]. Note that $\alpha_{(20)}$= 3.4×10$^{-3}$, and $\beta_{(20)}$=−7×10$^{-7}$.

Since R1=$Rh_{(t)}$, $$\begin{aligned} R1 &= Rh_{(20)} \cdot \{1+\alpha_{(20)} \cdot (t-20)+\beta_{(20)} \cdot (t-20)^2\} \quad (18) \\ &= Rh_{(20)} \cdot \{1+(3.2 \times 10^{-3}) \cdot (140-20)+(-7 \times \\ & \quad 10^{-7}) \cdot (140-20)^2\} \\ &= 1.40 \cdot Rh_{(20)} \end{aligned}$$

According to equation (17), $$\begin{aligned} \text{left member} &= (dRh_{(t)}/dt)/Rh_{(t)} \quad (19) \\ &= [Rh_{(20)} \cdot \{\alpha_{(20)}+2 \cdot \beta_{(20)} \cdot (t-20)\}]/(1.40 \cdot Rh_{(20)}) \\ &= \{\alpha_{(20)}+2 \cdot \beta_{(20)} \cdot (t-20)\}/1.40 \\ &= (3.4 \times 10^{-3} - 7 \times 10^{-7} \cdot 240)/1.40 \\ &= 2.31 \times 10^{-3} \end{aligned}$$

$$\begin{aligned} \text{right member} &= (d(RR2(T_{RR2})+R2)/dt)/(RR2(T_{R22})+R2) \quad (20) \\ &= [RR2_{(20)} \cdot \\ & \quad \{\alpha_{(20)}+2 \cdot \beta_{(20)} \cdot (T_{RR2}-20)\}]/(RR2(T_{RR2})+R2) \\ &= \{RR2_{(20)} \cdot (3.4 \times 10^{-3} - 7 \times 10^{-7} \cdot 80)\}/\{RR2_{(20)} \cdot \\ & \quad (1+3.4 \times 10^{-3} \cdot 40+1600 \cdot -7 \times 10^{-7})+R2\} \\ & \quad 3.344 \times 10^{-3} \cdot RR2_{(20)}/(1.135 \cdot RR2_{(20)}+R2) \end{aligned}$$

According to equations (19) and (20), $$3.344 \times 10^{-3} \cdot RR2_{(20)} - 2.31 \times 10^{-3} \cdot 1.135 \cdot RR2_{(20)} = 2.31 \times 10^{-3} \cdot R2 \quad (21)$$

According to equation (21), $$\begin{aligned} R2 &= (3.344 \times 10^{-3} \cdot RR2_{(20)}) - 2.31 \times 10^{-3} \cdot 1.135 \cdot \quad (22) \\ & \quad RR2_{(20)}/2.31 \times 10^{-3} \\ &= RR2_{(20)} \cdot (3.344 \times 10^{-3} - 2.31 \times 10^{-3} \cdot 1.135)/ \\ & \quad 2.31 \times 10^{-3} \\ &= 0.313 \cdot RR2_{(20)} \end{aligned}$$

In addition, since R3=(RR2($T_{RR2}$)+R2), $$\begin{aligned} R3 &= RR2_{(60)} + 0.313 \cdot RR2_{(20)} \quad (23) \\ &= (1.135+0.313) \cdot RR2_{(20)} \\ &= 1.45 \cdot RR2_{(20)} \end{aligned}$$

[Comparison with Prior Art 1]

The first to third embodiments have the following advantages as compared with prior art 1.

[Fast Response]

Since the TCD 21 is formed as a platinum thin film resistive element inside the diaphragm portion 31, and a compact mounting structure is realized, the volume of the measurement cell is small, and gas replacement can be quickly performed. For this reason, good response characteristics are attained.

Since the heating temperature $T_{Rh}$ of the TCD 21 is controlled to be kept at a constant value (the first and second embodiments), and the temperature difference between the heating temperature $T_{Rh}$ of the TCD 21 and the ambient temperature $T_{RR2}$ is controlled to be kept at a constant value (the first to third embodiments), thermal drifts of the TCD 21 are small, and the time required to stabilize the temperature is very short, thus realizing good response characteristics.

[Long Service Life]

Since the TCD 21 is formed as a platinum thin film resistive element in the diaphragm portion 31, this device is resistant to vibrations, and disconnection does not easily occur.

Since the heating temperature $T_{Rh}$ of the TCD 21 is controlled to be kept at a constant value (the first and second embodiments), and the temperature difference between the heating temperature $T_{Rh}$ of the TCD 21 and the ambient temperature $T_{RR2}$ is controlled to be kept at a constant value (the first to third embodiments), the TCD 21 undergoes a small temperature change, and is free from large thermal stress. In addition, resistance drifts and degradation are small, and the service life is long.

Since the heating temperature $T_{Rh}$ of the TCD 21 is controlled to be kept at a constant value (the first and second embodiments), and the temperature difference between the heating temperature $T_{Rh}$ of the TCD 21 and the ambient temperature $T_{RR2}$ is controlled to be kept at a constant value (the first to third embodiments), the diaphragm portion 31 is free from large thermal stress, and is protected. That is, since the diaphragm portion 31 has a three-layer structure, large thermal stress on the diaphragm portion 31 may cause peeling or deformation of the layers. In this embodiment, however, since no large thermal stress acts on the diaphragm portion 31, peeling or deformation of the layers does not occur.

[High Precision]

Since the temperature difference between the heating temperature $T_{Rh}$ and the ambient temperature $T_{RR2}$ is controlled to be a constant value, the thermal conductivity $\lambda m$ of a sample gas can be obtained with high precision. Since the thermal conductivity is a function of temperature, it is important to specify a temperature at which measurement is performed. In prior art 1, since the difference between the temperature of the TCD and the ambient temperature around the TCD changes, the thermal conductivity at a specific temperature cannot be measured, resulting in poor precision. In this embodiment, however, since the temperature difference between the heating temperature $T_{Rh}$ and the ambient temperature $T_{RR2}$ is controlled to be a constant value, the thermal conductivity at a specific temperature can be measured. This allows high-precision measurement.

[Comparison with Prior Art 2]

The first to third embodiments described above have the following advantages as compared with prior art

[Fast Response]

Since the TCD 21 is formed as a platinum thin film resistive element inside the diaphragm portion 31, and a compact mounting structure is realized, the volume of the measurement cell is small, and gas replacement can be quickly performed. For this reason, good response characteristics are attained.

[Long Service Life]

Since the TCD 21 is formed as a platinum thin film resistive element in the diaphragm portion 31, this device is resistant to vibrations, and disconnection does not easily occur.

[High Precision]

Since the temperature difference between the heating temperature $T_{Rh}$ and the ambient temperature $T_{RR2}$ is controlled to be a constant value, the thermal conductivity $\lambda m$ of a sample gas can be obtained with high precision.

In prior art 2, it is difficult to evenly keep the temperature of the vessel 6 at the predetermined temperature $t_2$°C, and the temperature measuring resistance wire 5 and the vessel 6 are not thermally insulated from each other. For this reason, the temperature measuring resistance wire 5 cannot be stably controlled to the temperature $t_1$°C. In addition, temperature control of the vessel 6 interferes with temperature control of the temperature measuring resistance wire 5, so their temperatures are not stable. In addition, since the temperature measuring resistance wire 5 is disposed in the center of the vessel 6, this device is easily affected by a gas flow. This causes a large measurement error.

In contrast to this, in this embodiment, since the TCD 21 is formed inside the diaphragm portion 31, and is thermally insulated from the base 30 on which the temperature sensor 22 is disposed, the heating temperature $T_{Rh}$ can be stably controlled to a constant temperature (the first and second embodiments). In addition, the temperature difference between the heating temperature $T_{Rh}$ and the ambient temperature $T_{RR2}$ can be controlled to a predetermined value (the first to third embodiments), and control of the heating temperature $T_{Rh}$ of the TCD 21 does not interfere with control of the ambient temperature $T_{RR2}$ around the base 30. Furthermore, in this embodiment, since the TCD 21 is formed inside the diaphragm portion 31 on the base 30 to be parallel to a gas flow in the chamber portion 106, the influence of a gas flow is small, and the thermal conductivity $\lambda m$ of a sample gas can be obtained with high precision.

[Comparison with Prior Art 3]

The first to third embodiments described above have the following advantages as compared with prior art

[Fast Response]

Since the TCD 21 is formed as a platinum thin film resistive element inside the diaphragm portion 31, and a compact mounting structure is realized, the volume of the measurement cell is small, and gas replacement can be quickly performed. For this reason, good response characteristics are attained.

Since the heating temperature $T_{Rh}$ of the TCD 21 is controlled to be kept at a constant value (the first and second embodiments), and the temperature difference between the heating temperature $T_{Rh}$ of the TCD 21 and the ambient temperature $T_{RR2}$ is controlled to be kept at a constant value (the first to third embodiments), thermal drifts of the TCD 21 are small, and the time required to stabilize the temperature is very short, thus realizing good response characteristics.

[Long Service Life]

Since the TCD 21 is formed as a platinum thin film resistive element in the diaphragm portion 31, this device is resistant to vibrations, and disconnection does not easily occur. In addition, since the TCD 21 is on a plane of the base 30 to be parallel to a gas flow, the TCD 21 does not receive fluid resistance much.

Since the heating temperature $T_{Rh}$ of the TCD 21 is controlled to be kept at a constant value (the first and second embodiments), and the temperature difference between the heating temperature $T_{Rh}$ of the TCD 21 and the ambient temperature $T_{RR2}$ is controlled to be kept at a constant value (the first to third embodiments), the TCD 21 undergoes a small temperature change, and is free from large thermal stress. In addition, resistance drifts are small, and the service life is long.

Since the heating temperature $T_{Rh}$ of the TCD 21 is controlled to be kept at a constant value (the first and second embodiments), and the temperature difference between the heating temperature $T_{Rh}$ of the TCD 21 and the ambient temperature $T_{RR2}$ is controlled to be kept at a constant value (the first to third embodiments), the diaphragm portion 31 is free from large thermal stress, and is protected.

[High Precision]

Since the temperature difference between the heating temperature $T_{Rh}$ and the ambient temperature $T_{RR2}$ is controlled to a constant value, the thermal conductivity $\lambda m$ of a sample gas can be obtained with high precision.

A method of calculating the quantity of heat of a sample gas by using the thermal conductivity $\lambda m$ calculated by the thermal conductivity calculating section 24 will be described next. Referring to FIG. 1, a quantity-of-heat calculating section 32 uses the thermal conductivity $\lambda m$ obtained by the thermal conductivity calculating section 24 to calculate a quantity of heat H of the gas according to equation (24) below:

$$H = -549.7 \times \lambda m + 35562.9 (kcal/N \cdot m^3) \quad (24)$$

City gas mainly consisting of a liquefied natural gas as a measurement gas is a lower hydrocarbon mixture mainly consisting of methane. Table 1 below shows the composition of this mixture. Referring to Table 1, the thermal conductivities are measured at a gas temperature of 114° C.

TABLE 1

| Hydro-carbon | Standard Concent-ration (%) | Concent-ration Range (%) | Calorific Value (kcal/N · m³) | Thermal Conductivity (mW/m · K) |
|---|---|---|---|---|
| $CH_4$ | 88.8 | 60.0–99.8 | 9540 | 47.3396 |
| $C_2H_6$ | 5.6 | 0.08–40.0 | 16830 | 34.078 |
| $C_3H_8$ | 3.7 | 0.01–5.0 | 24220 | 28.714 |
| $iC_4H_{10}$ | 1.8 | 2.5 or less | 31790 | 25.963 |
| others | 0.1 | — | | |

The calorific value of this measurement gas as a sample gas changes within the range of 9,500 to 12,000 kcal/N·m³.

The calorific value of the city gas mainly consisting of the natural gas made of the above components is about 11,000 kcal/Nm³. The relationship between the calorific value and thermal conductivity of the city gas can be approximated by a straight line connecting the thermal conductivities and calorific values of methane and ethane near the above calorific value. Equation (24) described above represents the straight line connecting the thermal conductivities and calorific values of methane and ethane.

Figure 7:
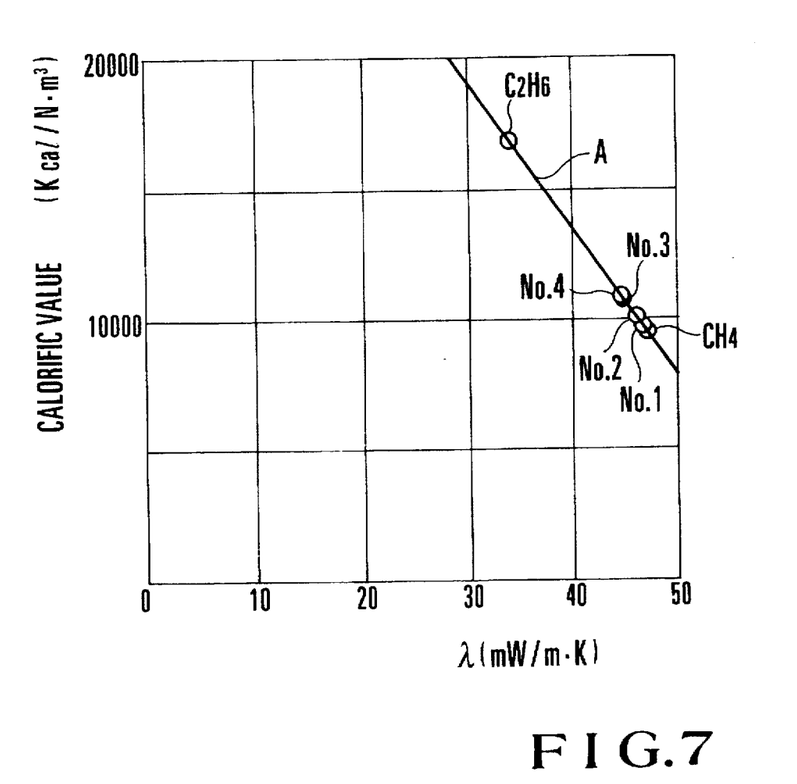
FIG. 7 is a graph showing the relationship between the measurement result of the thermal conductivity and the calorific value of a sample gas.

When the thermal conductivities of sample gases having the gas compositions in Table 2 were measured, the plotted points representing the measurement results and the calorific values are almost on a straight line A as shown in FIG. 7 based on equation (24).

TABLE 2

| Gas | $CH_4$ | $C_2H_6$ | $C_3H_8$ | $iC_4H_{10}$ | $nC_4H_{10}$ | Calorific Value (kcal/N · m³) |
|---|---|---|---|---|---|---|
| $CH_4$ | 100.00 | — | — | — | — | 9540 |
| NO. 1 | 98.51 | 0.50 | 0.99 | — | — | 9721 |
| NO. 2 | 96.00 | 1.00 | 3.00 | — | — | 10053 |
| NO. 3 | 90.75 | 2.95 | 5.09 | 0.61 | 0.60 | 10773 |
| NO. 4 | 86.98 | 10.00 | 1.99 | 0.51 | 0.52 | 10880 |
| $C_2H_6$ | — | 100.00 | | | | 16830 |

Instead of using equation (24), equation (25) as an approximation expression is established by the least squares method, thereby improving the precision.

$$H = -516.52 \times \lambda m + 33988.4 (kcal/N \cdot m^3) \quad (25)$$

Table 3 below shows the measurement results of the sample gases in Table 2, which were obtained by using equation (25). The maximum error was 30 kcal/Nm³.

TABLE 3

| Gas | Thermal Conduct-ivity (mW/m · K) | Calculated Calorific Value (kcal/Nm³) | Error (kcal/Nm³) |
|---|---|---|---|
| $CH_4$ | 47.3396 | 9536 | −4 |
| NO. 1 | 46.9492 | 9738 | −17 |
| NO. 2 | 46.3643 | 10040 | −13 |
| NO. 3 | 46.999 | 10745 | −28 |
| NO. 4 | 44.687 | 10906 | +26 |

As has been described above, according to the present invention, when a sample gas is supplied to the heating means (TCD) formed inside the diaphragm portion formed on the base, the heating means is deprived of heat proportional to the thermal conductivity of the gas. The amount of energy supplied to the heating means is controlled to keep the heating temperature of the heating means at a constant value, and the ambient temperature measured by the ambient temperature measuring means disposed on the base is kept at a constant value. While the ambient temperature and the heating temperature are kept at the constant values, the thermal conductivity of the sample gas is obtained on the basis of the amount of energy supplied to the heating means. Fast response and long service life can be attained. In addition, the thermal conductivity can be obtained with high precision.

In addition, the thermal conductivity of the sample gas is calculated by substituting the output voltage v, which is the voltage across the two ends of the heating elements while the ambient temperature and the heating temperature are kept at constant values, into a predetermined mathematical expression. For this reason, the output voltage/thermal conductivity characteristics need not be stored, and hence the memory capacity can be reduced.

Furthermore, the device constants in the mathematical expression need only be determined on the output voltages v measured by supplying first and second calibration gases to the heating means. For this reason, the time required for calibration and adjustment of the thermal conductivity type gas analyzer can be greatly shortened as compared with the conventional devices.

The ambient temperature and the heating temperature are respectively kept at 60° C. and 140° C. With this operation, in obtaining a predetermined mathematical expression, the thermal conductivities of the calibration gases which are obtained as physical data in advance at 100° C. can be used.

In addition, the thermal conductivity of the sample gas is obtained on the basis of the amount of energy supplied to the heating means while the ambient temperature and the heating temperature are kept at the constant values; fast response and long service life can be attained. Furthermore, the thermal conductivity can be obtained with high precision.

Moreover, the calorific value of a measurement gas can be obtained by measuring its thermal conductivity. In this case, the thermal conductivity scarcely changes within the pressure range near the atmospheric pressure. In general, this measurement is performed in a thermostat tank. For this reason, this device is not easily influenced by the surroundings and the measurement gas atmosphere, and hence can continuously measure the calorific value of the measurement gas.

What is claimed is:

1. A device for measuring the thermal conductivity of a sample gas, comprising:

a diaphragm formed on a base;

a thermal conductivity sensor formed on said diaphragm and coupled to said sample gas so that heat generated by said thermal conductivity sensor is transferred between said thermal conductivity sensor and said sample gas;

temperature measuring means, disposed on said base near said thermal conductivity sensor, for measuring an ambient temperature around said base, said temperature measuring means being thermally insulated from said thermal conductivity sensor;

means for supplying electrical energy to said thermal conductivity sensor;

means for controlling the electrical energy supplied to said thermal conductivity sensor so that a temperature difference between the temperature of said thermal conductivity sensor and said ambient temperature measured by said temperature measuring means is a constant, predetermined value;

thermal conductivity calculating means for calculating a thermal conductivity of the sample gas on the basis of the electrical energy supplied to said thermal conductivity sensor to achieve said temperature difference of said constant predetermined value.

2. A device according to claim 1, wherein said thermal conductivity calculating means calculates a thermal conductivity λm of the sample gas from an output voltage v generated across two ends of said thermal conductivity sensor according to the following mathematical expression:

$$\lambda m = (V^2/Rh - B)/A$$

where Rh is a resistance value of said thermal conductivity sensor, and A and B are intrinsic device constants.

3. A device according to claim 2, wherein the device constants A and B in the mathematical expression used in said thermal conductivity calculating means are set on the basis of output voltages measured by supplying to said thermal conductivity sensor first and second calibration gases, whose thermal conductivities are known.

4. A device according to claim 1, wherein when an output voltage generated across two ends of said thermal conductivity sensor and a resistance value of said heating means are respectively represented by v and Rh, said thermal conductivity calculating means obtains a thermal conductivity λm of the sample gas, which corresponds to the output voltage v in accordance with an intrinsic v–λm characteristic stored in advance.

5. A device according to claim 1 wherein said means for controlling the electrical energy supplied to said thermal conductivity sensor includes means for maintaining the temperature of said thermal conductivity sensor at a constant value and further includes means for controlling said ambient temperature to maintain said ambient temperature at a constant value.

6. A device according to claim 5, wherein said thermal conductivity sensor comprises a heating resistive element, and said means for controlling the thermal energy supplied to said thermal conductivity sensor controls a calorific value by changing an applied voltage as an amount of energy supplied to said heating resistive element.

7. A device according to claim 6, wherein said means for controlling electrical energy supplied to said thermal conductivity sensor comprises a resistance bridge including said heating resistive element, and a comparator for comparing voltages generated at first and second resistor connection points of said resistance bridge which oppose each other, and applying a voltage corresponding to the comparison result to another resistor connection point of said resistance bridge.

8. A device according to claim 1, further comprising quantity-of-heat calculating means for calculating a calorific value of the sample gas by using the thermal conductivity of the sample gas, which is calculated by said thermal conductivity calculating means, in a linear expression representing a relationship between the thermal conductivity and the calorific value of the sample gas constituted by a plurality of lower hydrocarbons.

9. A device according to claim 8, wherein the sample gas mainly consists of a natural gas, and the linear expression used by said quantity-of-heat calculating means is calorific value(Kcal/Nm$^3$) = −549.7 × thermal conductivity + 35562.9.

10. A device according to claim 8, wherein the sample gas mainly consists of a natural gas, and the linear expression used by said quantity-of-heat calculating means is calorific value (mcal/Nm$^3$) = −516.52 × thermal conductivity + 33988.4.

* * * * *